(12) United States Patent
Capelli

(10) Patent No.: US 7,147,845 B2
(45) Date of Patent: Dec. 12, 2006

(54) ANTIMICROBIAL SILVER ION COMPLEX RESINATES

(75) Inventor: Christopher C. Capelli, Pittsburgh, PA (US)

(73) Assignee: BioInterface Technologies, Inc., Houston, TX (US)

( * ) Notice: Subject to any disclaimer, the term of this patent is extended or adjusted under 35 U.S.C. 154(b) by 42 days.

(21) Appl. No.: 10/824,309

(22) Filed: Apr. 14, 2004

(65) Prior Publication Data

US 2004/0223944 A1 Nov. 11, 2004

Related U.S. Application Data

(60) Provisional application No. 60/464,867, filed on Apr. 23, 2003.

(51) Int. Cl.
| | |
|---|---|
| A61K 31/28 | (2006.01) |
| A61K 31/74 | (2006.01) |
| A61K 33/38 | (2006.01) |
| A61K 47/48 | (2006.01) |
| A61K 9/70 | (2006.01) |
| A61K 9/00 | (2006.01) |
| A01N 59/16 | (2006.01) |
| A01N 55/02 | (2006.01) |
| A01N 25/08 | (2006.01) |
| A61F 2/00 | (2006.01) |
| A61M 25/00 | (2006.01) |

(52) U.S. Cl. ............. 424/78.1; 424/400; 424/409; 424/411; 424/423; 424/443; 424/445; 424/484; 424/488; 424/78.12; 424/78.16; 424/618; 514/772; 604/544; 600/29

(58) Field of Classification Search ........ 424/400, 424/409, 411, 423, 78.1, 78.12, 78.16, 618, 424/443, 445, 484, 488; 514/772; 604/544; 600/29

See application file for complete search history.

(56) References Cited

U.S. PATENT DOCUMENTS

| | | | | |
|---|---|---|---|---|
| 2,434,190 | A | | 1/1948 | Barnes et al. ............... 210/24 |
| 2,692,855 | A | | 10/1954 | Juda ........................... 210/24 |
| 4,111,856 | A | * | 9/1978 | Haag et al. ................. 521/30 |
| 4,159,930 | A | * | 7/1979 | Degenkolb et al. ........ 205/569 |
| 5,326,567 | A | | 7/1994 | Capelli ...................... 424/405 |
| 5,429,819 | A | | 7/1995 | Oka et al. .................. 424/400 |
| 5,464,559 | A | | 11/1995 | Marchin et al. ............ 252/181 |
| 5,510,109 | A | | 4/1996 | Tomioka et al. ........... 424/421 |
| 5,605,632 | A | * | 2/1997 | Jansen et al. .............. 210/688 |
| 6,093,414 | A | | 7/2000 | Capelli ...................... 424/405 |
| 6,468,521 | B1 | | 10/2002 | Pedersen et al. .......... 424/78.17 |

FOREIGN PATENT DOCUMENTS

WO 99/13116 * 3/1999

OTHER PUBLICATIONS

The Merck Index, 12$^{th}$ edition, Merck & Co., Inc., Whitehouse Station, NJ, p. 369, item No. 2257.*
Lasko, Carol L. et al., "An investigation into the use of chitosan for the removal of soluble silver from industrial wastewater," Environmental Science and Technology, vol. 33(20), 1999, pp. 3622-3626.*
Chemical Abstracts, vol. 52, No. 14, p. 1958, abstract 11517g (Jul. 25, 1958).*

* cited by examiner

*Primary Examiner*—John Pak
(74) *Attorney, Agent, or Firm*—Medlen & Carroll, LLP

(57) ABSTRACT

The present invention relates to novel antimicrobial silver ion complex resinates. More particularly, the present invention contemplates silver ion complex resinate compositions comprising a silver-thiosulfate ion complex loaded onto an organic anion exchange resin. These silver thiosulfate ion complex resinate compositions are able to release stable antimicrobial silver ion complexes when placed in a saline environment. These antimicrobial silver-ion complex resinates are useful in the treatment and prevention of infections and diseases.

12 Claims, No Drawings

ANTIMICROBIAL SILVER ION COMPLEX RESINATES

This application claims the benefit of prov. appl No. 60/464,867 filed on Apr. 23, 2003.

FIELD OF INVENTION

The present invention relates to silver-based compositions attached to a resin and processes for making such resinate compositions having antibacterial, antiviral and/or antifungal activity. In one embodiment, the invention relates to a method of producing silver thiosulfate ion complex compositions and medical devices having a coating comprising such resinate compositions.

BACKGROUND

Topical antimicrobials are currently prescribed by healthcare providers to prevent and treat a variety of serious skin infections such as impetigo, infected diabetic ulcers, venous stasis ulcers, infected surgical wounds, burns, acne, psoriasis and other topical infections. Increasingly, topical antimicrobials that contain antibiotics are not effective against microbes which have developed drug resistance (i.e., antibiotic-resistant microbes).

Drug resistance is usually caused by a mutation within the microbe. When a colony of microbes is subjected to a dose of an antimicrobial, most of the bacteria die. However, occasionally some microbes, by chance, harbor mutant genes that render them resistant to the antimicrobial drug; Not only do these bacteria survive the antimicrobial treatment, but they transfer their "drug resistant" genes to their progeny (one bacterium can leave approximately 17,000,000 offspring within 24 hours). As a result, a specific antibiotic or antimicrobial used to treat an infection caused by that microbe may no longer be effective. Furthermore, once a microbe develops resistance to a specific antimicrobial, there is the possibility that the microbe will concomitantly be resistant to the entire class of antimicrobials.

Certain antimicrobials, especially antibiotics, are becoming increasingly ineffective due to the rapid increase in drug-resistant forms of microbes. For example, mupirocin ointment (Bactroban®, SmithKline Beecham) is a topical antimicrobial used most frequently for treatment of impetigo. Mupirocin has been shown to be highly effective against *Staphylococcus aureus, S. epidermidis, S. saprophyticus*, and *Streptococcus pyogenes*. Unfortunately, microbes frequently develop drug resistance to mupirocin.

What is needed are pharmaceutical compositions useful in the prevention and treatment of infections and diseases which comprise an antimicrobial agent and one or more medicinal agents and which remain antimicrobially active in an aqueous environment, and more specifically an aqueous environment that contains sodium chloride.

SUMMARY OF THE INVENTION

The present invention relates to silver-based compositions attached to a resin and processes for making such resinate compositions having antibacterial, antiviral and/or antifungal activity. In one embodiment, the invention relates to a method of producing silver thiosulfate ion complex compositions and medical devices having a coating comprising such compositions. In one embodiment, the silver thiosulfate ion complex is stabilized.

One aspect of the present invention contemplates novel antimicrobial silver ion complex resinates. In one embodiment, the present invention contemplates silver ion complex resinates compositions comprising a silver thiosulfate ion complex loaded onto an organic anion exchange resin. Preferably, these silver thiosulfate ion complex resinate compositions are stable in a saline environment and are capable of releasing antimicrobial silver ion. In one embodiment, the antimicrobial silver thiosulfate ion complex resinates are effective in the treatment and prevention of infections and diseases.

One aspect of the present invention contemplates a composition, comprising a silver thiosulfate ion complex bound to an anion exchange resin. In one embodiment, the resin comprises at least one quaternary amine attached to a polymer base. In one embodiment, the polymer base comprises polystyrene. In one embodiment, the polystyrene is in the form of beads. In one embodiment, the beads are less than approximately 0.8 mm in average diameter. In one embodiment, the quaternary amine is selected from the group consisting of triethylamine and triethylethanolamine. In one embodiment, the resin is cholestyramine.

One aspect of the present invention contemplates a wound dressing impregnated with a composition, comprising a silver thiosulfate ion complex bound to an anion exchange resin. In one embodiment, the wound dressing is selected from the group consisting of gauzes, compresses, hydrocolloids, xerogels and foams.

One aspect of the present invention contemplates a medical device impregnated with a composition, comprising a silver thiosulfate ion complex bound to an anion exchange resin. In one embodiment, the medical device is configured for placement inside a patient. In one embodiment, the medical device is selected from the group consisiting of implants, sutures and other materials left in a body cavity for a period of time. In one embodiment, the medical device is a catheter. In one embodiment, the catheter is a urinary catheter. In another embodiment, the medical device is selected from the group consisting of an ostomy appliance and an incontinent device.

One aspect of the present invention contemplates a method, comprising: a) providing; i) a patient exhibiting symptoms of infection; and ii) a composition, comprising a silver thiosulfate ion complex bound to an anion exchange resin; and b) administering said composition to said patient under conditions such that at least one symptom of said infection is reduced.

One aspect of the present invention contemplates a method, comprising: a) providing: i) a patient with a wound; and ii) a composition, comprising a silver thiosulfate ion complex bound to an anion exchange resin; and b) delivering said composition to said wound.

One aspect of the present invention contemplates a method, comprising: a) providing; i) a patient at risk for an infection; and ii) a composition, comprising a silver thiosulfate ion complex bound to an anion exchange resin; and b) administering said composition to said patient.

One aspect of the present invention contemplates a composition, comprising: a) a silver thiosulfate ion complex; and b) a resinate, wherein said complex is attached to said resinate. In one embodiment, said composition is photostable. In one embodiment, said silver thiosulfate ion complex is carrier-free. In one embodiment, said composition provides a controlled release of said silver thiosulfate ion complex. In one embodiment, said silver thiosulfate ion complex is stabilized. In one embodiment, said silver thiosulfate ion complex is stabilized by a sulfite. In one embodiment, said silver thiosulfate ion complex is stabilized by an amine. In one embodiment, said amine is selected from the group consisting of primary, secondary and tertiary. In one embodiment, said resinate comprises an organic anionic exchange resin. In one embodiment, said organic anionic exchange resin comprises functional groups selected from the group consisting of triethylamine and triethylethanolamine. In one embodiment, said resin is cholestyramine. In one embodiment, said composition further comprises a sulfite, wherein said sulfite stabilizes said silver thiosulfate ion complex. In one embodiment, said amine stabilized complex comprises a preservative agent. In one embodiment, said composition is stable in an aqueous environment. In one embodiment, said composition is stable in a saline environment. In one embodiment, said environment is a wound.

One aspect of the present invention contemplates a composition comprising a wound dressing impregnated with a silver thiosulfate ion complex resinate. In one embodiment, said resinate provides a controlled release of said silver thiosulfate ion complex. In one embodiment, said wound dressing is selected from the group consisting of gauze, compress, hydrocolloids, xerogels and foams. In one embodiment, said wound dressing comprises alginate. In one embodiment, a silver thiosulfate ion complex resinate is impregnated into a first component of a wound dressing, wherein said first component contacts said wound. In another embodiment, a silver thiosulfate ion complex resinate is impregnated into a second component of said dressing, wherein said second component is an adhesive.

One aspect of the present invention contemplates an apparatus comprising a medical device impregnated with a silver thiosulfate ion complex resinate. In one embodiment, said medical device further comprises a hydrophilic polymer, wherein said polymer is impregnated with said silver thiosulfate ion complex resinate. In one embodiment, said device comprises polymers selected from the group consisting of synthetic, animal, vegetable, polysaccharide, alginate, collagen, cellulose, polylactic acid, polyhydroxybutyrate, polyesters and polyvinyl alcohol, polyvinylpropylene, polyacrylates, polyurethanes, polymaleic acid, glucosamionoglycans, fibrin, copolymers and derivatives thereof. Preferably, said polymers are crosslinked, partially crosslinked or non-crosslinked. In one embodiment, said polymers are beads, wherein said beads are less than 0.8 mm in diameter. In one embodiment, said resinate provides a controlled release of a silver thiosulfate complex. In one embodiment, said released silver thiosulfate ion complex is carrier-free. In one embodiment, said medical device is selected from the group consisting of a wound dressing, an ostomy appliance and an incontinent device. In another embodiment, said medical device is a urinary catheter impregnated with an anhydrous polymer. In one embodiment, said medical device is selected from the group consisting of implants, sutures and other materials left in a body cavity for a period of time. In another embodiment, said silver thiosulfate ion complex is photostable. In one embodiment, said silver thiosulfate ion complex is stablized. In one embodiment, said silver thiosulfate complex is stabilized by a sulfite. In one embodiment, said silver thiosulfate ion complex is stabilized by an amine. In one embodiment, said stabilizing amine is selected from the group consisting of primary, secondary and tertiary. In one embodiment, said amine stabilized complex comprises a preservative agent. In one embodiment, said preservative agent comprises the chemical compound class of alcohols. In one embodiment, said composition is stable in an aqueous environment. In one embodiment, said composition is stable in a saline environment. In one embodiment, said environment is a wound.

One aspect of the present invention contemplates a method, comprising: a) providing; i) a patient exhibiting symptoms of a microbiological infection; and ii) a resinate comprising a silver thiosulfate ion complex, wherein said complex retains antimicrobiological activity; and b) administering said resinate to said patient under conditions such that at least one symptom of said infection is reduced. In one embodiment, said antimicrobiological activity is selected from the group comprising antibiotic, antiviral and antifungal.

One aspect of the present invention contemplates a method, comprising: a) providing: i) a patient exhibiting a wound having a significant amount of bodily fluid seepage; and ii) a resinate comprising a silver thiosulfate ion complex, wherein said complex retains antimicrobiological activity; and b) administering said resinate to said patient under conditions such that said complex is delivered to said wound and said bodily fluid seepage within said wound is reduced. In one embodiment, said method further comprising placing a wound dressing impregnated with said resinate onto said wound.

One aspect of the present invention contemplates a method, comprising: a) providing; i) an anionic exchange resin; and ii) an aqueous stabilized silver thiosulfate ion complex solution; b) attaching a first half of said silver thiosulfate ion complex solution to said resin during a first equilibrim stage to form a partially loaded resinate; and c) attaching a second half of said silver thiosulfate ion complex solution to said partially loaded resinate during a second equilibrium stage to form a fully loaded resinate. In one embodiment, said fully loaded resinate is at least 50% of a theoretical loading capacity. In one embodiment, said resin and said silver thiosulfate ion complex are attached when in equal concentration. In one embodiment, said resin comprises a strong base comprising a quaternary amine and a polymer base backbone.

One aspect of the present invention contemplates a process, comprising: a) mixing a silver halide and silver nitrate to form a precipitate in an aqueous solution; b) agitating said preciptate with sodium thiosulfate to form a silver thiosulfate ion complex; c) separating said aqueous solution from said sodium thiosulfate to form a dry powder; and d) dissolving said dry powder with sodium sulfite and trihydroxymethyl-aminomethane to form a stabilized silver thiosulfate amine complex solution. In one embodiment, said stabilized silver thiosulfate amine complex is carrier-free.

Definitions

To facilitate understanding of the invention set forth in the disclosure that follows, a number of terms are defined below.

As used herein, the term "topically" means application to the surface of the skin, mucosa, viscera, etc.

As used herein, the term "topically active drugs" indicates a substance or composition which elicits a pharmacologic response at the site of application but which is not necessarily an antimicrobial agent.

As used herein, the term "systemically active drugs" is used broadly to indicate a substance or composition which will produce a pharmacologic response at a site remote from the point of application.

As used herein, the term "medical devices" includes any material or device that is used on, in, or through a patient's body in the course of medical treatment for a disease or injury. Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, IUD's and IUD strings, diaphragms and condoms.

As used herein, the term "silver thiosulfate ion complex", refers to silver-containing materials obtained by adding a silver halide to an aqueous solution and then adding a thiosulfate salt to the solution. Preferably, the silver complexes of the present invention are derived from the complexation of silver cations from silver halides (preferably silver chloride) with anions from the sodium thiosulfate salt. In one embodiment, the molar ratio of the thiosulfate anions to the silver cations is preferably at least 1:1 and more preferably at least 1.3:1. It is desirable that the silver thiosulfate ion complexes are solid and essentially pure, i.e., they do not contain significant amounts of waste salts or other substances that interfere with their antimicrobial activity; in addition, they do not require carrier particles. In particular, the term "silver thiosulfate ion complexes" refers to the silver-containing material produced by a process disclosed in U.S. Pat. No. 6,093,414 to Capelli. (herein incorporated by reference)

As used herein, the term "stabilized" refers to any silver thiosulfate complex that, when redissolved in an aqueous solution containing sodium chloride (i.e., for example, a wound environment), is more resistant to degradation then silver thiosulfate complexes made without a stabilizing agent (i.e., for example, an amine).

As used herein, the term "amine-stabilized" silver thiosulfate ion complex refers to any compound containing a primary, secondary or tertiary amine that, when in association with a silver thiosulfate ion complex prevents the appearance of marked degradation for at least 19 hours in an aqueous solution at 50° C.

As used herein, the term "preservative agent" refers to any compound that prolongs the ability of an amine compound to prevent the appearance of marked degradation.

As used herein, the term "marked degradation" refers to the appearance of a significant amount of black precipitation in a solution containing a silver ion complex.

As used herein, the term "impregnated" refers to any interaction between a medical device and a silver thiosulfate complex contemplated by this invention. Impregnation may be reversible or irreversible. Such impregnation may be synonymous with "attachment" and includes, but is not limited to, covalent bonding, ionic bonding, Van de Waal forces or friction, and the like. A compound is impregnated to a medical device if it is attached, coated, in suspension with, in solution with, mixed with, etc.

As used herein, the term "wound" denotes a bodily injury with disruption of the normal integrity of tissue structures. In one sense the term is intended to encompass the term "surgical site". In another sense, the term is intended to encompass the terms "sore", "lesion", "necrosis" and "ulcer" which may be used interchangeably. Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. Examples of wounds which can be prevented and/or treated in accordance with the present invention are, but not limited to, aseptic wounds, contused wounds, incised wounds, lacerated wounds, non-penetrating wounds (i.e., wounds in which there is no disruption of the skin but there is injury to underlying structures), open wounds, penetrating wound, perforating wounds, puncture wounds, septic wounds, subcutaneous wounds, etc. Examples of sores are, but not limited to, bed sores, canker sores, chrome sores, cold sores, pressure sores etc. Examples of ulcers are, but not limited to, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous clear, symptomatic ulcer, trophic ulcer, tropical ulcer, venereal ulcer, e.g. caused by gonorrhoea (including urethritis, endocervicitis and proctitis). Conditions related to wounds or sores which may be successfully treated according to the invention are burns, anthrax, tetanus, gas gangrene, scarlatina, erysipelas, sycosis barbae, folliculitis, impetigo contagiosa, or impetigo bullosa, etc.

As used herein, the term "loading capacity" refers to the quantification of the attachment or impregnation of a silver ion complex to a resin. Loading capacities are empirically determined through controlled experimentation. Relative loading capacities are expressed by a percentage of theoretical maximum expected under ideal laboratory conditions. As such, loading capacities may vary according to changes in conditions such as, but not limited to, temperature, pH, incubation time, concentrations of reagents and reagent quality.

As used herein, the term "polymer base" refers to any molecule comprising multiple subunits that have a substantial degree of chemical similarity. For example, in one embodiment, a polymer base is a form of polystyrene. In particular, one form of a polymer base is an anionic exchange resin.

As used herein, the term "hydrophilic polymer" refers to any molecule comprising multiple subunits that is miscible in an aqueous solution. One form of a polymer may be a "bead", which may be either solid or hollow, and take any shape desired. In particular, beads are one the order of millimeters in diameter.

As used herein, the term "infection" refers to any microbial invasion of living tissue that is deleterious to the organism. Microbial infections may be caused by microorganisms including, but not limited to, bacteria, viruses and fungi.

As used herein, the term "solvent" refers to any material that is capable of mixing with another solution to extract specific compounds. For example, an amine and a solvent may be added to an aqueous solution, followed by the separation of an immiscible bilayer.

As used herein, the term "matrix" refers to any combination of materials that results in a solid or semisolid structure.

As used herein, the term "anion exchange resin" refers to any polymer molecular structure that is able to absorb drugs that are negatively charged (i.e. drugs comprising an anion). For example, silver thiosulfate ion is a negatively charged complex and therefore are attracted to resins having a strong cationic base (i.e., $—N^+(R)_3$). In one embodiment, a strong cationic base resin is cholestyramine. Preferably, the binding of compatible molecules may be selectively removed by chemical solutions that differ in characteristics such as, but not limited to, pH, ionic strength, concentration and salt content.

As used herein, the term "amine-stabilized" silver thiosulfate ion complex refers to any compound containing a primary, secondary or tertiary amine that, when in association with a silver thiosulfate ion complex prevents the appearance of marked degradation for at least 19 hours in an aqueous solution at 50° C. An "amine" is any nitrogen atom comprising at least one substituent.

As used herein, the term "low level of electrolytes" refers to electrolytes in a concentration equivalent to less than 0.9% saline (i.e., NaCl) solution and preferably less than 0.1% saline solution.

As used herein, the term "high level of electrolytes" refers to electrolytes in a concentration equivalent to, or greater than, 0.9% saline (i.e., NaCl) solution.

As used herein, the term "resin" refers to a polymer base that does not have attached silver thiosulfate ion complexes.

As used herein, the term "resinate" refers to a polymer base that does have attached silver thiosulfate ion complexes. Preferably, the bound silver thiosulfate ion complexes are released from the resinate in a controlled manner in a carrier-free form.

As used herein, the term "carrier" refers to any compound or molecule that facilitates the production of silver ion complexes by a process that is not contemplated by this invention. Specifically, the production of silver ion complexes contemplated by this invention do not require carriers and are thus designated as "carrier-free".

DETAILED DESCRIPTION OF THE INVENTION

The present invention relates to silver-based compositions attached to a resin and processes for making such resinate compositions having antibacterial, antiviral and/or antifungal activity. In one embodiment, the invention relates to a method of producing silver thiosulfate ion complex compositions and medical devices having a coating comprising such compositions.

The present invention also relates to stabilized silver thiosulfate ion complexes that have improved water stability (i.e., maintaining antimicrobial activity in an aqueous environment). More particularly, the present invention contemplates amine stabilized silver thiosulfate ion resinates comprising a resin, a silver thiosulfate ion complex and an amine stabilizing agent, wherein said stabilized silver thiosulfate ion resinate has increased stability when in an aqueous environment. In one embodiment, the amine stabilized silver thiosulfate ion resinate comprises a preservative capable of stabilizing said amine.

The antiseptic activity of silver compounds is a known property. Although it is not necessary to understand the mechanism of an invention, it is believed that the bacteriostatic and fungistatic effect of a silver thiosulfate ion complex contemplated by the present invention is caused by a silver ion. For example, one compound known in the art that has been clinically useful is silver nitrate. Aqueous silver nitrate solutions of 0.5% –1% show disinfectant properties and are used for preventing infections in burns or for prophylaxis of neonatal conjunctivitis. Another silver compound, silver sulfadiazine, has a pronounced antibacterial effect. It is known in the art that the inherent antibacterial property of sulfadiazine molecule is enhanced by complexation with a silver ion. In contrast to silver nitrate, the solubility of the silver sulfadiazine complex is low, and hence, both the silver ion and sulfadiazine ion are present in low concentrations but may be present over longer periods of time. Silver sulfadiazine is intensively used in the treatment of wounds, in particular burns, under the trademarks Silvadene® and Flamazine®. Silver-protein combinations are yet another antiseptic formulation which have been used in low concentrations as eye drops.

Bacteriostatic silver ion compositions are marketed in various medical devices. One example is a wound dressing having an activated charcoal cloth dressing (Actisorb®, Johnson & Johnson). Another example is a wound dressing of modified pigskin impregnated with soluble silver compound intended for treatment of burns (EZ-Derm®, Genetic Laboratories). The antiseptic properties of silver compounds is known and disclosed in various patents and publications.

A specific advantage in using the silver ion as a bacteriostatic agent is the general lack of formation of bacterial tolerance to the compound. This is in contrast to many types of antibiotics (i.e., development of "antibiotic resistance). A major drawback of using ionic silver for bacteriostatic purposes is the marked degradation (i.e., appearance of a dark stain) of the silver ion complex. It is believed that this marked degradation is mediated by a chemical reduction of the silver ion to free silver. Such staining has been reported to give potentially permanent pigmentation of the skin, the so-called argyria. It is commonly recognized that silver containing compounds will also discolor under the influence of light and/or heat. Additionally, radiation sterilization may lead to silver ion composition color changes, irrespective of the use in a solution, cream or gel or a medical device. These phenomena result in the avoidance of silver ion complexes by those skilled in the art when contemplating medical device sterilization. Furthermore, such medical or cosmetic products often comprise antibacterial compositions wherein discoloration is highly undesirable or unacceptable to the user.

Recently, the principles of antimicrobial photostable metal-based compositions have been disclosed. Capelli, U.S. Pat. No. 5,326,567; Oka, U.S. Pat. No. 5,429,819; and Tomioka, U.S. Pat. No. 5,510,109 (all incorporated herein by reference). Specifically, the '567 discloses a unique "host-guest" relationship between silver ions and acyclic polyethers accomplished through the use of excess of halide ions. Additionally, the '819 patent describes a porous particulate carrier requirement for photostable compositions comprising a complexation of silver ion with a thiosulfate salt. More recently, a photostable composition comprising a complex of silver ion with a thiosulfate salt has been disclosed that does not require a porous particulate carrier. Capelli, U.S. Pat. No. 6,093,414 (hereby incorporated by reference). The silver compositions of the '414 patent are unusually stable in the presence of both heat and light. However, in the presence of water, or any aqueous solution containing bases or polymers, even a silver thiosulfate ion complex undergoes marked degradation. Although it is not necessary to understand the mechanisms involved for successful use of the invention, it is believed that this silver thiosulfate ion complex degradation occurs when the thiosulfate ligand component of the silver thiosulfate ion complexes experiences a chemical breakdown. The effect of this chemical process results in an overall destabilization and degradation of the silver thiosulfate ion complexes with concomitant loss of medicinal activity.

The improvement of silver ion composition stability in an aqueous environment is known by the formation of a complex with a primary, secondary or tertiary amine. Pedersen, U.S. Pat. No. 6,468,521 (herein incorporated by reference). Although the '521 patent discloses that the production of these amine stabilized silver complexes utilize ". . . readily soluble salts like the nitrate, lactate, or acetate or more heavily soluble salts like the halogenides such as the chloride or bromide.", there is no teaching regarding the stability of the amine stabilized silver complexes in an aqueous environment particularly wherein the aqueous environment contains a significant amount of sodium chloride. In fact, the silver ion complexes, as taught by the '521 patent, are unstable in the presence of sodium chloride ions (e.g., ions derived from dissolved sodium chloride). That is to say, in aqueous solutions containing chloride ions, the silver in the silver ion complex immediately precipitates as silver chloride. Silver chloride retains a minimal amount of antimicrobial activity due to the low dissociation rate of silver ions from silver chloride. However, the antimicrobial activity of silver chloride is poor relative to soluble silver salts or silver ion complexes.

One aspect of the present invention contemplates the production of silver thiosulfate ion complexes obtained by adding a silver halide, e.g., silver chloride, to an aqueous solution and then adding a thiosulfate salt, e.g., sodium thiosulfate, to the solution. Preferably, a silver thiosulfate ion complex of the present invention is derived from the complexation of a silver cation from a silver halide (e.g., for example, silver chloride) with an anion from a sodium thiosulfate salt; the molar ratio of thiosulfate anions to silver cations is preferably at least 1:1 and more preferably at least 3:1. It is desirable that the silver thiosulfate ion complexes are solid and essentially pure (i.e., they do not contain significant amounts of waste salts or other substances that interfere with their antimicrobial activity) and, in addition, they do not require carrier particles (i.e., carrier-free). Solution purity is particularly important when loading said compositions into an organic anion exchange resin contemplated by this invention. Waste salts or other substances interfere with, and limit, the loading of anion exchange resins.

Though the benefit provided by the complexes of the present invention is not limited by an understanding of the precise nature of the complexes, the chemical formula of a silver thiosulfate ion complex formed when a large excess of thiosulfate salt is used is believed represented by $[Ag(S_2O_3)_3]^{5-}$. By comparison, the chemical formula of a silver thiosulfate ion complex formed when only a small excess of thiosulfate salt is used is believed represented by $[Ag_2(S_2O_3)_3]^{4-}$. In one embodiment, the present invention contemplates a silver thiosulfate ion complex represented by $[Ag_2(S_2O_3)_3]^{4-}$. Preferably, any silver thiosulfate ion complex contemplated by this invention is a relatively pure solid form, stable, highly water soluble and antimicrobially active.

One aspect of the present invention contemplates an improvement upon the compositions and methods by which medical devices are impregnated with antimicrobial compounds. Currently, there is a problem disclosed in the prior art involving an excessive release of silver ion complex compositions incorporated into medical devices such as, but not limited to, wound dressings, ostomy appliances, incontinence devices and other medical devices or hydrophilic coatings. This excessive silver ion release results in tissue irritation and lack of patient compliance resulting in a discontinuation of use of the medical device. Furthermore, when excess bodily fluid is present (i.e. significant presence of sodium chloride), the silver ion is quickly rendered ineffective and the antimicrobial protection is short lived. To overcome this problem, one aspect of the present invention contemplates silver thiosulfate ion complexes that are attached to resins.

The attachment of silver ion compositions to carriers (i.e., such as silica gels) are known to provide the capability for sustained release of antibacterial and antifungal compounds. Tomioka, U.S. Pat. No. 5,510,109 (herein incorporated by reference). The '109 patent discloses a porous silica gel or zeolite particle carrier having antibacterial and antifungal activity that may or may not be coated with a coating material. The disclosed antibacterial and antifungal composition consists of at least one metal complex salt and plant extracts. Silica gel is disclosed as a preferred composition due to its relatively larger surface area and greater transparency than zeolite. The '109 further discloses a method of preparation that includes an aqueous or an alcohol solution of the antibacterial and antifungal material with the porous carrier that is subsequently dried. In this step, it is taught that it is preferable to use 2–10 parts by weight of the antibacterial or antifungal material for every 100 parts by weight of the carrier.

A porous particulate carrier (Type B silica gel: mean particle diameter of 1–10 µm) is also disclosed to attach an antiviral composition comprising a silver thiosulfate salt and at least one of metal thiosulfate complex salt. Oka, U.S. Pat. No. 5,429,819. The '819 patent further teaches that in order to provide slow release and long acting properties of the composition, the silver thiosulfate salt/metal silver thiosulfate complex salt to porous particulate carrier ratio should be 1–10:100 (w/w).

Both the '109 and '819 patents depend upon porous particulate silica gel carriers wherein the antimicrobial silver is attached by absorption into the carrier pores. Two problems arise by using this composition. First, the amount of silver that may be absorbed into the carrier is limited by steric hinderance within the fixed volume of the carrier pores. This limitation is implicitly admitted by both Tomioka and Oka wherein a large excess of carrier must be used relative to the amount of antimicrobial compound (i.e., the preferred amount of antimicrobial silver compound is "1–10 parts by weight, and more preferably as 2–5 parts by weight, for 100 parts of the carrier"). Second, the delivery of silver is dependent upon the physicochemical characteristics of the immediate environment and is simply a result of diffusion of the silver compound from the porous particulate carrier. For example, in an aqueous environment, the release of the silver compound can be rapid. The only approach to reduce the rate of release in previously disclosed silver compounds is to limit the rate of diffusion out of the carrier. This approach requires additional procedures in the production of these compositions.

For example, one approach to reduce diffusion requires special coatings applied to the porous particulate carrier that hinder the diffusion of the silver ion from the porous particles. Specifically, the '819 discloses just such a layer of a coating material: "By forming said coating material layer, the above-mentioned antibacterial and antiviral composition becomes to have a preferred slow releasing property. Therefore, it has a scarce detrimental effect for contaminating the environment."

Surprisingly, it has now been found that silver compositions in the form of antimicrobial silver thiosulfate ion complex resinate compositions, when placed in a saline environment, release silver ion complexes that are stable, carrier-free and antimicrobially active.

One aspect of the present invention contemplates silver thiosulfate ion complexes as disclosed in the '414 patent that are attached to resins. In one embodiment, the silver thiosulfate ion complex resinate compositions are stabilized using sulfite compounds. In one embodiment, said sulfite is selected from the group consisting of sodium sulfite, potassium sulfite, sodium bisulfite, potassium bisulfite, sodium metabisulfite, and potassium metabisulfite. In another embodiment, the silver thiosulfate ion complex resinate compositions are stabilized using amine compounds. In another embodiment, said agent is selected from the group consisting of methylamine, ethylamine, propylamine, butylamine and tri-hydroxymethylaminomethane. Preferably, stabilized silver thiosulfate complex compositions (i.e., sulfite or amine) are preserved by agents represented by the chemical compound class of alcohols. In one embodiment, said preservation agent is selected from the group consisting of glycerol, methanol, ethanol, propanol, butanol and polyvinylalcohol.

It is known that silvered anion exchange resins may be produced by using silver nitrate to load a resin with silver ions. Barnes et al., U.S. Pat. No. 2,434,190. Metallic silver is then generated, by treatment with a reducing agent, such as potassium metabisulfite. The silvered resin is used for disinfecting water. Alternatively, a silvered cationic exchange resin may also be produced to disinfect water. Juda, U.S. Pat. No. 2,692,855. As described in the '855 patent, a cationic exchange of silver ions for hydrogen ions results from treatment with a solution of a silver salt, thereby producing a silvered resin capable of disinfecting water.

A chelating resin using polystyrene divinyl benzene copolymer having iminodiacetate is also disclosed for water treatment. Marchin, U.S. Pat. No. 5,464,559. The iminodiacetate groups, bound to porous granules of the resin, chelate silver ions that interact with the passage of water through the resin. The effectiveness of this invention is limited to a loading capacity of 0.5 mole silver ions per mole of iminodiacetate. This low threshold for an effective loading capacity is to ensure that water treated by said chelating resin remains substantially free of silver ions (i.e., the chelated silver ions do not dissociate and contaminate the water).

The silver ion compositions discussed above used in loading ionic resins for water purification are silver salts such as silver nitrate. These previously disclosed resins are capable of loading and releasing silver ion into the environment. However, a known major problem regarding these disclosed silvered resins is that the silver is released as silver ion. In environments containing halides (i.e., for example, chloride, bromide or iodide) released silver ions immediately complex with halides and precipitate out of solution. These silver halide precipitates have minimal antimicrobial activity. In environments where the use of the silver resins is not expected to be exposed to salts (i.e., purification of drinking water), the release of silver ions does not present a problem. However, in environments containing substantial amounts of salts (i.e., for example, environments comprising bodily fluids), the antimicrobial efficacy of the previously disclosed silvered resins is minimized. Finally, a further problem exists with these disclosed silvered resins when made with a silver salt as they tended to discolor when exposed to ambient light with a concomitant loss in antimicrobial activity. From an esthetic standpoint, their appearance generally results in an avoidance of their use.

A surprising and unexpected finding of the present invention is that silver ion complexes in the form of silver thiosulfate ion complexes can bind to anion exchange resins to form silver thiosulfate ion complex resinates. In one embodiment, silver thiosulfate ion complex resinates are resistant to discoloration when exposed to ambient light.

A further surprise is that the release of the silver from the silver ion complex resinates is stable in aqueous environments containing salts. For example, in an aqueous environment containing sodium chloride (such as found in bodily fluids), the antimicrobial silver released from the resinate does not precipitate in the form of silver chloride. Although it is not necessary to understand the mechanism for a successful use of an invention, it is believed that stable silver ion is released from resinates as contemplated by the present invention in the form of a silver thiosulfate ion complex. In one embodiment, antimicrobial efficacy of silver thiosulfate ion is maintained in the environments (i.e., wounds, colostomy sites, etc.) where previously disclosed silver ion compositions are known to lose antimicrobial activity.

One aspect of the present invention contemplates a silver thiosulfate ion complex attachment to a cholestyramine resin thus forming an insoluble polymer base to create a silver thiosulfate ion complex resinate. In one embodiment, silver thiosulfate ion complexes are released from resinates in vivo. In another embodiment, silver thiosulfate ion complex resinates reach a first stable release rate of said silver thiosulfate ion complex in solutions having a high electrolyte concentration (i.e., for example, in secreted bodily fluids into a wound). In another embodiment, silver thiosulfate ion complex resinates reach a second stable release of said silver thiosulfate ion complex in solutions having a low electrolyte concentration (i.e., for example, in a healing wound), wherein said second release rate is significantly less than said first release rate. In one embodiment, silver ion released into a saline environment from a resinate is in the form of a silver thiosulfate ion complex, wherein said released silver ion complex is stable and remains antimicrobially active.

As described above, inorganic carriers disclosed previously, such as silica gel, are inadequate to accommodate an impregnation of large concentrations of silver ion complexes that are capable of controlled release. Surprisingly, the present invention contemplates silver ion complex resinates comprising organic anion exchange resins. In one embodiment, these resinates are formed by loading silver ion complexes onto resins by ionic coupling. Preferably, the loading capacity ratio of silver ion complex to resin ranges from approximately between 1–100:100 parts (w/w), but more preferably between 50–100:100 parts (w/w). Simply stated, resinates are formed by loading from anywhere between 1–100 parts of silver compound by weight for every 100 parts of resin. Optimally, the present invention contemplates an equal ratio of silver ion complexes to resin. In one embodiment, antimicrobial silver ion complexes are released from a resinate by an exchange for a chloride ion present in the immediate environment. As a result, silver ion complex release from resinates is not a matter of simple diffusion. Conversely, the present invention contemplates an ability to control release rates of silver ion complexes from any resinate by variation of environmental counter ion concentrations.

In one embodiment, the present invention contemplates an organic anion exchange resin having a strong base comprising a quaternary amine attached to a polymer base backbone (e.g., for example, polystyrene beads). Although it is not necessary to understand the mechanism involved in the success of an invention, it is believed that a strong base resin is preferred over a weak base resin because, a strong base resin's effectiveness is not dependent on environmental pH. Conversely, a weak base resin typically requires a slurry composition or an environment of pH 7 or less. Furthermore, the typical ionic capacity of any strong base resin is greater than that of any weak base resin, such that a lower volume of resin is required. Additionally, strong base resins are more widely used, thus more available and economical than weak base resins. Alternatively, gel-based resins and macroporous resins are both contemplated by this invention to substitute for a strong base resins.

One aspect of the present invention contemplates impregnation of medical devices with silver ion resinates comprising polymer beads of less than 0.8 mm in average diameter. In one embodiment, suitable resinates include, but are not limited to, strong base resinates comprising Type I (Triethylamine functional groups) and Type II (triethyl ethanolamine functional groups). Preferably, the silver ion resinates comprise a macroporous matrix of polystyrene, cross-linked with 8–10% divinyl benzene. In one embodiment, one specific strong base anion exchange silver ion resinate includes, but are not limited to, Dowex-41, Dowex MSA-1 (Type I), Dowex-42, Dowex MSA-2 (Type II), gel-type resin 21K (all of which are manufactured by Dow Chemical); Amberlite IRA900C, Amberlite IRA-904 (Type I), Amberlite IRA-910 (Type II) (all of which are manufactured by Rohm & Haas); A500, A500 UC (both manufactured by Purolite); Lewatit-600 and MP500 (both manufactured by Bayer). In one embodiment, the present invention contemplates a silver ion resinate comprising a cholestyramine resin and a silver thiosulfate ion complex. Cholestyramine resins are anion exchange resins in the chloride form, insoluble and strongly basic. A preferred cholestyramine resin is Cholestyramine Resin USP (Duolite AP143/1083; Rohin and Haas Company). In one embodiment, cholestryramine resin is loaded with at least 47.75 w/w % of a silver thiosulfate ion complex.

One aspect of the present invention contemplates loading a silver thiosulfate ion complex onto an anion exchange resin, wherein the loading capacity of said anion exchange resin is maximized. For example, batch equilibration is contemplated to load silver thiosulfate ion complexes onto anion exchange resin powder.

One advantage of using anion exchange resins is their known potential for high capacity loading of silver ion complexes. Cholestyramine (an anion exchange resin), for example, under ideal laboratory conditions has a maximum achievable exchange capacity for sodium glycocholate of 1.8 to 2.2 g/g. Practically, however, the capacity of cholestyramine resin, when loading a drug, is normally between 5% and 50% of this maximum. Regardless, the potential loading capacity for an anion exchange resin is still substantially higher than organic porous carriers (i.e, silica gels) that are well known in the art.

One aspect of the present invention contemplates a method of attaching silver thiosulfate ion complexes on a resin comprising multiple equilibrium stages. In one embodiment, attaching silver thiosulfate ion to a resin thus forming a partially loaded resinate occurs during a first equilibrium stage. In another embodiment, attaching silver thiosulfate ion to a partially loaded resinate thus forming a completely loaded resinate occurs during at least a second equilibration. Preferably, any method comprising multiple equilibrium stages adds the total available amount of silver ion complex in equal amounts at each equilibrium stage. Subsequent to each equilibrium stage, each resulting partially loaded resinate is separated from its respective liquid phase. Although it is not necessary to understand the mechanism of an invention, it is believed that loading resin(ate)s using multiple equilibrium stages is an effective means of achieving maximum loading of a silver thiosulfate ion complex onto a resin(ate) while maintaining minimum loss of silver ion into the liquid phase; specifically during the final equilibrium stage. In order to determine a quantitative value for any loading capacity a carefully controlled, empirically derived, laboratory experiment is required operating under precise loading and releasing conditions. In general, however, the presence of a relatively high silver thiosulfate ion complex concentration in the loading solution, in the presence of a minimum of competing anions, will favor higher absorption capacities.

One aspect of the present invention contemplates a controlled release composition comprising an antimicrobial silver ion complex resinate composition. In one embodiment, a coating controls release of silver thiosulfate ion from a resinate complex. In vivo, resinate pharmacokinetics determined by measuring attached silver ion rate of release and bioavailability reflect the ability of a resinate to release a known amount if silver ion complex. The present invention contemplates that the rate of silver thiosulfate ion complex resinate release is controlled by diffusion rates through the polymer base and the concentration of electrolytes in the immediate environment. In one embodiment, a high release rate of silver thiosulfate ion complex from a resinate results when in the presence of a high level of electrolytes in the immediate environment. In another embodiment, a low release rate of silver thiosulfate ion complex from a resinate results when in the presence a low level of electrolytes in the immediate environment. In one embodiment, a high level of electrolytes is present within a wound having a significant amount of bodily fluid seepage. In one embodiment, a low level of electrolytes is present within a healing wound, wherein bodily fluid seepage is reduced. This phenomenon is of great practical advantage, for example, in a wound where there is a significant amount of seepage of bodily fluid, increased amounts of silver thiosulfate ion complex is released to provide increased antimicrobial protection. When the wound begins to heal, however, the amount of seepage begins to slow and, concomitantly, the amount of silver released from resinate slows (i.e., the resinate rate of release is reduced). As a result, medical devices which release varying amounts of stable antimicrobial silver can be produced using this invention.

The present invention contemplates antimicrobial silver ion complex resinate compositions having antibacterial, antiviral and/or antifungal activity that are used in wound care products and dressings, ostomy appliances, incontinence devices, or other medical devices and hydrophilic coatings. In one embodiment, antimicrobial silver ion complex resinate compositions are impregnated into hydrophilic polymers of medical devices. In another embodiment, these resinate impregnated medical devices have a stable and controlled release of antimicrobial silver ion into the immediate environment.

Hydrophilic polymers suitable for controlling the rate of silver ion complex release from resinates contemplated by the present invention include, but are not limited to, synthetic hydrophilic polymers and derivatives of animal or vegetable hydrophilic polymers. In one embodiment of the invention, a hydrophilic polymer comprises polysaccharides, alginates, collagen and the like. In one preferred embodiment, a polysaccharide is a cellulose derivative. In one embodiment, a cellulose derivative is selected from a group comprising sodium carboxymethylcellulose and hydroxyethylcellulose. In one embodiment, an alginate is sodium alginate or any other compatible salt. In one embodiment, a collagen is porcine collagen. Other preferred polymers include, but are not limited to, polylactic acid, polyhydroxybutyrates or similar polyesters, polyvinyl alcohol, polyvinylpropylene (PVP), polyacrylates, hydrophilic polyurethanes, polymaleic acid and polymers of natural origin like glucosaminoglycans, collagen and fibrin or the like as well as copolymers or derivatives thereof. Preferably, hydrophilic polymers are crosslinked, partially crosslinked or non-crosslinked.

One aspect of the present invention contemplates a wound dressing impregnated with silver thiosulfate ion resinate compositions. In one embodiment, a wound dressing comprises material selected from the group comprising traditional gauzes and compresses, hydrocolloid dressings, xerogels and foams. In one embodiment, a silver thiosulfate ion complex resinate is impregnated into a first component of a wound dressing by dissolution into water or other suitable aqueous solutions, wherein said first component contacts said wound. In another embodiment, a silver thiosulfate ion complex resinate is impregnated into a second component of said dressing, wherein said second component contacts a surface surrounding said wound (e.g., for example, an adhesive composition) by a manner known per se.

Another aspect of the present invention contemplates a method incorporating a silver thiosulfate ion complex resinate composition into alginate fiber dressings or similar dressings. In one embodiment, the method comprises adding silver ion resinates to an alginate solution before processing into a fibrous material. In one embodiment, added silver ion resinate comprises a powder formed by grinding a lyophilized or spray-dried resinate composition. Alginate wound dressings may comprise a silver thiosulfate ion complex resinate impregnated into an adhesive for fixing the dressing to the wound site or into another part of the dressing, for instance a foam pad.

One aspect of the present invention contemplates antimicrobial silver ion complex resinate compositions and formulations thereof having antibacterial, antiviral or antifungal activity, wherein the compositions are used in the area of human or veterinary medicine. In one embodiment, antimicrobial silver thiosulfate ion complex resinate compositions are incorporated into medical devices, including medical implants, wound care devices, body cavity and personal protection devices, and the like. In one embodiment, a silver thiosulfate ion complex resinate composition is incorporated within an anhydrous polymer and impregnates a urinary catheter, wherein the resinate-polymer prevents infection. In another embodiment, a silver resinate composition is impregnated into cosmetics and personal care products thereby making them resistant to antimicrobial contamination. Examples of such cosmetics include, but are not limited to, lipsticks and glosses, lip pencils, mascaras, eye liners, eye shadows, moisturizers, liquid and powder makeup foundations, powder and cream blushes, perfumes, colognes, various creams and toners, etc., and assorted applicators like combs, brushes, sponges, and cotton swabs and balls, and examples of personal care products include deodorants, razors, shaving creams, shampoos, conditioners, various hair treatments like mousses and sprays, toothpastes, mouthwashes, dental flosses and tapes, sunscreens, moisturizers, tampons, sanitary napkins, panty shields, diapers, baby wipes, facial tissues, toilet tissues, etc.

Other embodiments of the present invention contemplate medical devices suitable for impregnation by silver ion resinate compositions. In one embodiment, an impregnated medical device selected from the group comprising a foam or other vaginal insert for use in the continence care, condoms, male external urine catheters, skin adhesives etc. In another embodiment, an impregnated medical device does not necessarily provide direct contact with the body, wherein such medical devices include, but are not limited to, incontinence pad and ostomy pouch powders for removal of odor.

One aspect of the present invention contemplates a medical device comprising an antimicrobial silver thiosulfate ion resinate complex composition, wherein said medical device is in contact with internal bodily tissues for a period of time. In one embodiment, said medical device is selected from the group comprising implants, sutures or materials that for a period will be left in body cavities. In one embodiment, said medical device contacts internal bodily tissues during surgery. In another embodiment, said medical device contacts internal bodily tissues after surgery. Preferably, antimicrobial silver thiosulfate ion resinates prevent infections known to develop as a result of surgical procedures. In one embodiment, the present invention contemplates implantation of a medical device impregnated with a silver thiosulfate ion complex simultaneously with systemic antibiotic prophylactic treatment and proper antiseptic skin treatment. In another embodiment, the present invention contemplates contacting internal bodily tissues with a medical device impregnated silver thiosulfate ion complex simultaneously with systemic antibiotic prophylactic treatment and proper antiseptic skin treatment. The present invention offers an advantageous alternative to known compositions comprising silver ion because the present contemplated resinate compositions have broad antiseptic properties and are stable during storage and use.

In one embodiment, the present invention contemplates a medical device comprising an impregnation or coating comprising an antimicrobial silver thiosulfate ion complex resinate composition wherein silver thiosulfate ion complexes are further complexed with a primary, secondary or tertiary amine. In one embodiment, said amine is selected from the group comprising methylamine, ethylamine, propylamine, butylamine and tri-hydroxymethyl aminomethane.

Furthermore, the present invention contemplates a method of producing compositions having antibacterial, antiviral and/or antifungal activity comprising an antimicrobial silver thiosulfate ion complex resinate wherein the silver thiosulfate complex is dissolved in water. In one embodiment, the method further comprises adding an amine in molar excess wherein the resulting solution is incubated for approximately between 1 to 100 hours, and preferably for approximately between 12–24 hours. In another embodiment, the method further comprises adjusting the pH using an acid to between approximately 6.5–9.0. In one embodiment, the method further comprises adding a hydrophilic polymer that is optionally dried and/or micronized.

Still further, the present invention contemplates a method of using an antimicrobial silver ion complex resinate composition wherein a silver thiosulfate ion resinate complex is further complexed with a primary, secondary or tertiary amine. In one embodiment, an amine silver thiosulfate ion resinate complex is associated with at least one hydrophilic polymer, wherein said composition has antibacterial, antiviral and/or antifungal activity. In one embodiment, said method further comprises impregnating a medical device to produce a wound dressing, an ostomy appliance, an incontinence device, other medical devices or hydrophilic coatings.

The invention is explained more in detail in the working examples below disclosing embodiments and properties of compositions of the invention. It is evident that many variations may be made without diverging from the invention the scope of which is set forth in the appended claims.

Experimental

In the disclosure which follows, the following abbreviations apply: L (liters); ml (milliliters); µl (microliters); g (grams); mg (milligrams); µg (micrograms); mol (moles); mmol (millimoles); µmol (micromoles); cm (centimeters); mm (millimeters); nm (nanometers); ° C. (degrees Centigrade); MW and M.W. (molecular weight); N (normal); w/w (weight-to-weight); w/v (weight-to-volume); min. (minutes); Sigma-Aldrich (Milwaukee, Wis.); Columbus (Columbus Chemical Industries; Columbus, Wis.); No. (number); ICP (inductively coupled plasma); CFU (colony forming units); PEG (polyethylene glycol); MHM (Mueller Hinton Medium); ZOI (zone of inhibition); ATCC.

EXAMPLE 1

Process for Making Silver Thiosulfate Ion Complexes

This example illustrates a process for producing silver thiosulfate ion complexes useful for this invention.

The silver thiosulfate ion complexes were produced by first making a silver chloride precipitate in an aqueous (i.e., deionized water) solution (hereafter, "silver chloride precipitate/aqueous solution"). The silver chloride precipitate/aqueous solution was made by mixing 20 ml of 1 mmol/ml silver nitrate (Aldrich) with 22 ml of 1 mmol/ml sodium chloride (Aldrich) in a 500 ml separatory funnel. To the resulting silver chloride precipitate/aqueous solution was added 60 ml of 1 mmol/ml sodium thiosulfate (Columbus). The resulting mixture was agitated by shaking the separatory funnel until all of the silver chloride precipitate was dissolved.

The silver thiosulfate ion complexes produced were separated by adding 200 ml of ethyl alcohol to the funnel. Upon addition of the ethyl alcohol, the solution became cloudy and separated into two separate phases. The two phases were separated using the separatory funnel. The weight of the material in the phase containing the silver thiosulfate ion complexes was approximately 17 g. This phase was then treated by adding 70 ml ethyl alcohol and 40 ml of acetone to make the silver thiosulfate ion complexes essentially anhydrous. After sitting overnight, the silver thiosulfate ion complexes were in the form of a pure, white solid material in the bottom of the container. Thereafter, the solvent was decanted and the white solid was dried in an oven (i.e., for example, at 62° C.) until the solid was able to be ground into a fine white powder using a mortar and pestle. The weight of the dried silver thiosulfate ion complexes was 10.03 g.

EXAMPLE 2

Control Solution A: Silver Nitrate Solution

Silver nitrate in the amount of 0.588 mmol (100 mg) was dissolved in 10 ml of distilled water. The 1% silver nitrate solution was clear and colorless.

EXAMPLE 3

Test Solution B: Silver Thiosulfate Ion-Complex Solution

A silver thiosulfate ion-complex solution was made by dissolving 0.587 mmol (315 mg) of silver thiosulfate ion complex (nominal M.W. of 537) from Example 1 into 10 ml of distilled water. The resulting solution was clear and colorless.

EXAMPLE 4

Control Solution C: Silver Nitrate-THAM Solution

This example provides an a non-thiosulfate based silver ion complex. Specifically, this example describes a silver compound in the form of a complex with a primary, secondary or tertiary amine.

A silver nitrate-THAM complex solution was made using previous disclosed methods. Pedersen, U.S. Pat. No. 6,468,521. Briefly, silver nitrate in the amount of 0.588 mmol (100 mg) was dissolved in 10 ml of distilled water. Tri-hydroxymethyl-aminothmethane (THAM) (M.W. of 121) in the amount 2.057 mmol (249 mg) was added to the silver nitrate solution. The silver nitrate-THAM (1:3.5) complex was equilibrated overnight at ambient temperature. The resulting solution was clear and colorless.

EXAMPLE 5

Test Solution D: Sulfite Stabilized Silver Thiosulfate Ion Complex Solution

A silver thiosulfate ion-complex solution was prepared by dissolving 0.587 mmol (315 mg) of silver thiosulfate ion complex (nominal M.W. of 537) from Example 1 into 10 ml of distilled water. To this solution was added 100 mg of sodium sulfite (Sigma-Aldrich) to aid in stabilizing the silver thiosulfate ion complex. The resulting solution was clear and colorless.

EXAMPLE 6

Test Solution E: Sulfite Stabilized Silver Thiosulfate-THAM Solution

A sulfite stabilized silver thiosulfate-THAM solution contemplated by this invention was prepared.

Silver thiosulfate powder from Example 1 in the amount 0.587 mmol (315 mg) was dissolved in 10 ml of distilled water. To this solution was added 100 mg of sodium sulfite (Sigma-Aldrich) to aid in stabilizing the silver thiosulfate ion complex.

Tri-hydroxymethyl-aminothmethane (THAM) (M.W. of 121) in the amount 2.057 mmol (249 mg) was next added to the sulfite stabilized silver thiosulfate solution. The sulfite stabilized silver thiosulfate-THAM solution was equilibrated overnight at ambient temperature. The resulting solution was clear and colorless.

EXAMPLE 7

Preparation of the Silver Thiosulfate Ion Complex Resinates

This example provides one embodiment for the preparation of a silver thiosulfate ion complex resinate. Three silver thiosulfate ion complex resinates contemplated by this invention (i.e., Test Resinate B, Test Resinate D and Test Resinate E) were prepared by loading a cholestyramine resin with silver thiosulfate ion complex solutions from their respective solutions (supra).

The silver thiosulfate ion complex resinates were prepared by adding 5 ml of: i) solution B prepared in accordance with Example 3; ii) solution D prepared in accordance with Example 5; and iii) solution E prepared in accordance with Example 6 into separate vials containing 50 mg of cholestyramine resin (Sigma-Aldrich). The mixtures were then left to equilibrate over a 12 hour period. The vials containing the mixtures were shaken periodically through this equilibration period. After the 12 hour period, this first supernatant was drained from the vials. An additional 3.5 ml of Test Solutions B, D and E was then added to each respective containing the Test Solution/cholestyramine resin. The mixtures again were then left to equilibrate over a 12 hour period. The vials containing the mixtures were shaken periodically through this equilibration period. After the 12 hour period, this second supernatant was drained from the vials leaving behind a cholestyramine resin "loaded" with its respective Test Solution (i.e., a Test Resinate).

Each "loaded" Test Resinate was then washed with distilled water to remove non-loaded silver thiosulfate ion complexes. Distilled water (5 ml) was added to each sample of the Test Resinate, shaken and left to settle for a period of 1 hour. This wash solution was then drained and discarded. The Test Resinate was washed again ("$2^{nd}$ Wash") as outlined above. However, this wash solution was drained and tested for the presence of silver thiosulfate-ion complex. The respective Test Resinates were given a final wash with ethanol (5 ml) and then left to dry.

The color of the resulting Test Resinates ranged from all-white to light-tan. No discoloration (i.e., marked degradation) was noted when stored in ambient light.

EXAMPLE 8

Preparation of the Control Resinates

This example describes the preparation of Silver Salt Control Resinates or Non-Thiosulfate Silver Ion Complex Control Resinates for comparison to the three Test Resinates prepared in Example 7.

The Control Resinates were prepared by loading cholestyramine resin with either: i) a Silver Nitrate Salt Control Solution A prepared in accordance with Example 2; or ii) a Silver Nitrate-THAM Control Solution C prepared in accordance with Example 4. The Control Resinates were made by adding 5 ml of Control Solutions A and C into separate vials, each containing 50 mg of cholestyramine resin (Sigma-Aldrich). The mixtures were then left to equilibrate over a 12 hour period. The vials containing the mixtures were shaken periodically through this equilibration period. After 12 hours this supernatant was drained from the vials. An additional 3.5 ml of Control Solutions A or C, respectively, was then added to the Control Solution/cholestyramine resin. The mixtures again were then left to equilibrate over a 12 hour period and periodically shaken. After 12 hours this supernatant was drained from the vials leaving behind a cholestyramine resin "loaded" with its respective Control Solution (i.e., a Control Resinate).

Each "loaded" Control Resinate was then washed with distilled water to remove the silver ion complex that was not loaded into the resin. Distilled water (5 ml) was added to each sample of the Control Resinates. The mixture was shaken and left to settle for a period of 1 hour. This wash was drained and discarded. The Control Resinates were washed again ("$2^{nd}$ Wash") as outlined for the first wash. However, the wash was drained and tested for residual silver thiosulfate complex. Each Control Resinate was given a final wash with ethanol (5 ml) and then left to dry.

Control Resinates A turned a blue-gray color upon exposure to ambient light over a period of a few hours.

EXAMPLE 9

Antimicrobial Activity of the Test and Control Solutions

This example compares the release of silver compounds from the silver ion resinates by determining the in vitro antimicrobial activity of the Test Solutions (i.e., Examples 3, 5 and 7) and Control Solutions (i.e., Examples 2 and 4).

Filter paper discs (7 mm diameter) were soaked with the Test Solutions (B, D or E) or the Control Solution (A and C) from the examples above. The antimicrobial studies were performed by first plating S. aureus (ATCC 29213) or E. coli (ATCC 225922) on tryptic soy agar. A disc containing either a Test Solutions or a Control Solution was placed on each of these microbial lawns. The culture plates were incubated at 37° C. overnight. The zone of microbial growth inhibition (ZOI) was measured from the edge of each filter disc. The averaged results from two trials, measured in millimeters, are shown below in Table 1. The larger the measured ZOI, the greater the antimicrobial effect. The results of this study are as follows:

TABLE 1

Antimicrobial Activity of Solutions

| Sample | S. Aureus | E. Coli |
| --- | --- | --- |
| Control Solution A (1% AgNO$_3$) | 1.5 mm | 1.0 mm |
| Control Solution C (Ag-THAM) | 2.25 mm | 1 mm |
| Test Solution B (Ag-Thiosulfate) | 10.5 mm | 5.75 mm |
| Test Solution D (Ag-Thiosulfate-Sulfite) | 7.5 mm | 15 mm |
| Test Solution E (Ag-Thiosulfate-THAM) | 10 mm | 8 mm |

The results from Table 1 illustrate that both the Control Solutions and the Test Solutions generate sufficient antimicrobial activity to generate a measurable ZOI. The zones of microbial growth inhibition for the Test Solutions B, D & E, however, were much greater than the zones resulting from the Control Solutions A & C despite the fact that concentration of free silver ion is equivalent to approximately 1% silver nitrate in both groups. The minimal ZOI generated by the silver nitrate and silver-THAM complex Control Solutions is believed to be because the free silver ion precipitates with the salts in the culture media. As a result, the ZOI data demonstrates that free silver ion in the Control Solutions is ineffective as an antimicrobial. On the other hand, the Test Solutions comprising silver thiosulfate ion complexes allow the complexed silver ion to interact with microbes while simultaneously protecting them from inorganic precipitation. Therefore, the Test Solutions have a large ZOI thus demonstrating a high antimicrobial efficacy. This test mimics the real world environment of a wound site where there are compounds and salts in the fluid that can make antimicrobial silver ineffective.

EXAMPLE 10

Antimicrobial Activity of the Resinates

This examples demonstrates the antimicrobial activity of resinates contemplated by the present invention. Specifically, the in vitro antimicrobial activities of Test Resinates from Example 7 were compared to the Control Resinates from Example 8.

Briefly, 1 ml of saline was added to each vial of resinate. At the 1 hour and 3 hour time points, filter paper discs (7 mm diameter) were soaked with the saline supernatant to test for the release of antimicrobial silver. As a comparison, filter paper discs were also made using the $2^{nd}$ wash solution from Example 7 and Example 8.

The antimicrobial studies were performed by first plating S. aureus (ATCC 29213) or E. coli (ATCC 225922) on tryptic soy agar. Filter discs soaked in the control and test solutions as described above placed on each of these microbial lawns. The culture plates were incubated at 37° C. overnight. The zone of microbial growth inhibition (ZOI) was measured from the edge of each filter disc. The results in millimeters for two trials were averaged. The larger the measured ZOI, the greater the antimicrobial effect. The results of this study are as follows:

TABLE 2A

Antimicrobial Activity Comparison: S. aureus

| Sample | $2^{nd}$ Wash | Saline 1 hour | Saline 3 hour |
|---|---|---|---|
| Control Resinate A (1% AgNO$_3$) | 0 mm | 0 mm | 0 mm |
| Control Resinate C (Ag-THAM) | 0 mm | 0 mm | 0 mm |
| Test Resinate B (Ag-Thiosulfate) | 1.25 mm | 2.25 mm | 3 mm |
| Test Resinate D (Ag-Thiosulfate-Sulfite) | 0 mm | 1.5 mm | 1 mm |
| Test Resinate E (Ag-Thiosulfate-THAM) | 1 mm | 3 mm | 2 mm |

TABLE 2B

Antimicrobial Activity Comparison: E. coli

| Sample | $2^{nd}$ Wash | Saline 1 hour | Saline 3 hour |
|---|---|---|---|
| Control Resinate A (1% AgNO$_3$) | 0 mm | 0 mm | 0 mm |
| Control Resinate C (Ag-THAM) | 0 mm | 0 mm | 0 mm |
| Test Resinate B (Ag-Thiosulfate) | 2.5 mm | 1.75 mm | 2 mm |
| Test Resinate D (Ag-Thiosulfate-Sulfite) | 0 mm | 2 mm | 2.75 mm |
| Test Resinate E (Ag-Thiosulfate-THAM) | 1.5 mm | 2.5 mm | 3.75 mm |

The results from Table 2A and 2B illustrate that resinates loaded with Test Solutions (i.e., silver thiosulfate complexes) have antimicrobial activity as demonstrated by the ZOI study. Resinates loaded with Control Solutions (i.e., silver nitrate or silver-THAM complex) have minimal if any antimicrobial activity as demonstrated by the ZOI. The results of this study demonstrate that silver in the form of silver thiosulfate ion complexes can be slowly released from resinates over time in a saline environment. On the other hand, silver in the form of silver nitrate or silver-THAM complexes show no antimicrobial activity when placed in a saline environment.

EXAMPLE 11

Antimicrobial Activity of the Silver Resinate Post-Wash Supernatants

The in vitro antimicrobial activities of post-wash supernatants from Test Resinates made according to Example 7 were further compared to the post-wash supernatants from Control Resinates made according to Example 8.

As described in Example 7 and Example 8, after each resinate had soaked in saline solution for 3 hours, the first saline supernatant was drained and discarded. Then each resinate was subjected to two 5 ml distilled water washes. Following the water washes, one ml of fresh saline was added to each vial of resinate. After 3 hours of incubation, filter paper discs (7 mm diameter) were soaked with the saline supernatant to test for the post-wash release of antimicrobial silver. Antimicrobial studies were performed according to Example 10 using E. coli (ATCC 225922) on tryptic soy agar. Briefly, a disc containing the Test Solutions or Control Solutions were placed on each of these microbial lawns. The culture plates were incubated at 37° C. overnight. The zone of microbial growth inhibition (ZOI) was measured from the edge of each filter disc. The results in millimeters from two trials were averaged. The larger the measured ZOI, the greater the antimicrobial effect. The results of this study are as follows:

TABLE 3

Antimicrobial Activity of Solutions: Post-Wash Supernatant

| Sample | E. Coli |
|---|---|
| Control Solution A (1% AgNO$_3$) | 0 mm |
| Control Solution C (Ag-THAM) | 0 mm |
| Test Solution B (Ag-Thiosulfate) | 0.75 mm |
| Test Solution D (Ag-Thiosulfate-Sulfite) | 1.25 mm |
| Test Solution E (Ag-Thiosulfate-THAM) | 1 mm |

The results from Table 3 illustrate that supernatants incubated with resinates loaded with Test Solutions (i.e., silver thiosulfate complexes) have antimicrobial activity as demonstrated by the ZOI study even after multiple washes with distilled water and saline. Resinates loaded with Control Solutions (i.e., silver nitrate or silver-THAM complex) have minimal, if any, antimicrobial activity as demonstrated by the ZOI. The results of this study further demonstrate that silver in the form of silver thiosulfate ion complexes can be slowly released from resinates over time in a saline environment. Even after multiple washes with distilled water and saline, the Test Resinates are able to release silver in great enough amounts so as to produce antimicrobial results. On the other hand, silver in the form of silver nitrate or silver-THAM complexes showed no antimicrobial activity when placed in a saline environment.

I claim:

1. A composition comprising a silver thiosulfate ion complex bound to a cholestyramine resin, wherein said complex comprises a thiosulfate ion-to-silver molar ratio that is selected from the group consisting of at least 1:1, at least 1.3:1 and at least 3:1.

2. A wound dressing impregnated with a composition comprising a silver thiosulfate ion complex bound to an anion exchange resin.

3. The wound dressing of claim 2, wherein said wound dressing is selected from the group consisting of gauzes, compresses, hydrocolloids and xerogels.

4. An apparatus comprising a medical device impregnated with a composition comprising a silver thiosulfate ion complex bound to an anion exchange resin.

5. The apparatus of claim 4, wherein said medical device is configured for placement inside a patient.

6. The apparatus of claim 5, wherein said medical device is selected from the group consisting of implants, sutures and other materials left in a body cavity for a period of time.

7. The apparatus of claim 5, wherein said medical device is a catheter.

8. The apparatus of claim 7, wherein said catheter is a urinary catheter.

9. The apparatus of claim 5, wherein said medical device is selected from the group consisting of an ostomy appliance and an incontinent device.

10. A method, comprising:
a) providing;
   i) a patient exhibiting symptoms of infection; and
   ii) a composition comprising a silver thiosulfate ion complex bound to an anion exchange resin; and
b) administering said composition to said patient under conditions so that at least one symptom of said infection is reduced.

11. A method, comprising:
a) providing:
   i) a patient with a wound; and
   ii) a composition comprising a silver thiosulfate ion complex bound to an anion exchange resin; and
b) delivering said composition to said wound.

12. A method, comprising:
a) providing;
   i) a patient at risk for an infection; and
   ii) a composition comprising a silver thiosulfate ion complex bound to an anion exchange resin; and
b) administering said composition to said patient.

* * * * *